US009560976B2

(12) United States Patent
Lane et al.

(10) Patent No.: US 9,560,976 B2
(45) Date of Patent: Feb. 7, 2017

(54) MEDICAL INSTRUMENT WITH REMAINING VISITS INDICATOR

(71) Applicant: Welch Allyn, Inc., Skaneateles Falls, NY (US)

(72) Inventors: John A. Lane, Weedsport, NY (US); Craig M. Meyerson, Syracuse, NY (US); David M. Fallat, Auburn, NY (US); Vuong B. Nguyen, Liverpool, NY (US); Shawn C. St. Pierre, Syracuse, NY (US); Kenneth V. Coon, III, Jordan, NY (US); Michael D. Garrant, Marcellus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 472 days.

(21) Appl. No.: 14/079,388

(22) Filed: Nov. 13, 2013

(65) Prior Publication Data

US 2015/0133742 A1    May 14, 2015

(51) Int. Cl.
| | |
|---|---|
| *A61B 5/02* | (2006.01) |
| *A61B 5/0205* | (2006.01) |
| *A61B 5/1455* | (2006.01) |
| *A61B 5/021* | (2006.01) |
| *A61B 5/00* | (2006.01) |
| *G06F 19/00* | (2011.01) |

(52) U.S. Cl.
CPC .......... *A61B 5/02055* (2013.01); *A61B 5/021* (2013.01); *A61B 5/14552* (2013.01); *A61B 5/742* (2013.01); *A61B 2560/0204* (2013.01); *A61B 2560/0437* (2013.01); *G06F 19/327* (2013.01); *G06F 19/3412* (2013.01)

(58) Field of Classification Search
CPC . A61B 5/02055; A61B 5/14552; A61B 5/742; A61B 5/021; A61B 2560/0204; A61B 2560/0437; G06F 19/327; G06F 19/3412
See application file for complete search history.

(56) References Cited

U.S. PATENT DOCUMENTS

| | | | |
|---|---|---|---|
| 4,693,119 A | 9/1987 | Johnson | |
| 7,612,999 B2 * | 11/2009 | Clark | A61B 5/0002 248/918 |
| 7,657,273 B2 | 2/2010 | Haartsen | |
| 8,214,566 B2 * | 7/2012 | Edwards | A61B 1/00105 709/208 |
| 8,332,342 B1 | 12/2012 | Saha et al. | |
| 2008/0312852 A1 * | 12/2008 | Maack | A61N 1/3708 702/63 |
| 2009/0062887 A1 | 3/2009 | Mass | |

(Continued)

FOREIGN PATENT DOCUMENTS

JP           11289677 A        10/1999

OTHER PUBLICATIONS

Cardiac Science, Instruction Manual for Cardiac Science 5300 and Cardiac Science 5350 Vital Signs Monitor (70-00582-01 A), date accessed May 14, 2013, 182 pgs.

(Continued)

*Primary Examiner* — Rex R Holmes
(74) *Attorney, Agent, or Firm* — Merchant & Gould P.C.

(57) ABSTRACT

A medical instrument includes a remaining visits indicator. The remaining visits indicator visually identifies a number of patient visits that can be completed before recharging the medical instrument.

21 Claims, 10 Drawing Sheets

(56) References Cited

U.S. PATENT DOCUMENTS

| | | |
|---|---|---|
| 2011/0040572 A1 | 2/2011 | Chmiel et al. |
| 2011/0153154 A1 | 6/2011 | Hagenbuch |
| 2012/0003933 A1 | 1/2012 | Baker |
| 2012/0095312 A1 | 4/2012 | Ramey et al. |
| 2012/0210325 A1 | 8/2012 | De Lind Van Wijngaarden |
| 2012/0215075 A1 | 8/2012 | Surace et al. |
| 2014/0148718 A1* | 5/2014 | Stickney ................ A61B 5/044 600/523 |

OTHER PUBLICATIONS

Welch Allyn, Vital Signs Monitor 300 Series Directions for Use, date accessed May 14, 2013, 108 pgs.

* cited by examiner

MEDICAL INSTRUMENT WITH REMAINING VISITS INDICATOR

BACKGROUND

Batteries are commonly used to power mobile medical instruments to permit the mobile medical instruments to be moved independent of stationary power sources.

A visual indicator is sometimes provided on mobile medical instruments to identify the amount of charge remaining in the batteries. Such an indicator may indicate whether the battery is fully charged, partially charged, or nearly depleted, for example.

SUMMARY

In general terms, this disclosure is directed to a medical instrument with a remaining visits indicator. In one possible configuration and by non-limiting example, the remaining visits indicator visually identifies an estimated number of patient visits that can be completed before recharging the medical instrument. Various aspects are described in this disclosure, which include, but are not limited to, the following aspects.

One aspect is a mobile medical instrument configured for use by a caregiver during patient visits, the mobile medical instrument comprising: a measuring device configured to perform physiological measurements on patients during the patient visits; one or more energy storage devices configured to store energy therein to power the measuring device when performing the physiological measurements; and a display device configured to generate a remaining visits indicator identifying an estimated number of patient visits that can be completed by the instrument before the energy stored in the one or more energy storage devices is depleted.

Another aspect is a method of operating a mobile medical instrument, the method comprising: determining a quantity of charge stored in one or more energy storage devices; determining historical patient visit charge consumption; computing an estimated number of remaining patient visits until the stored charge is depleted; and generating a remaining visits indicator identifying the estimated number of remaining patient visits.

A further aspect is a mobile medical instrument configured for use by a caregiver during patient visits, the mobile medical instrument comprising: a measuring device, the measuring device comprising: a housing; a processing device; peripheral components controlled by the processing device and including one or more sensors configured to cooperate with the measuring device to measure one or more physiological characteristics of patients, the peripheral components including a thermometer, a blood pressure cuff, and a pulse oximeter; a first energy storage device; and a display device operatively connected to the processing device and operable to generate a remaining visits indicator, the remaining visits indicator identifying an estimated number of patient visits that can be completed by the measuring device before recharging the mobile medical instrument; a mobile stand, the mobile stand comprising: a wheeled base comprising a plurality of wheels; a support structure coupled to the wheeled base and configured to support the measuring device in an elevated position; a second energy storage device contained in the support structure; and power supply electronics electrically coupled to the second energy storage device and configured to deliver power from the second energy storage device to the measuring device.

DETAILED DESCRIPTION

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Figure 1:
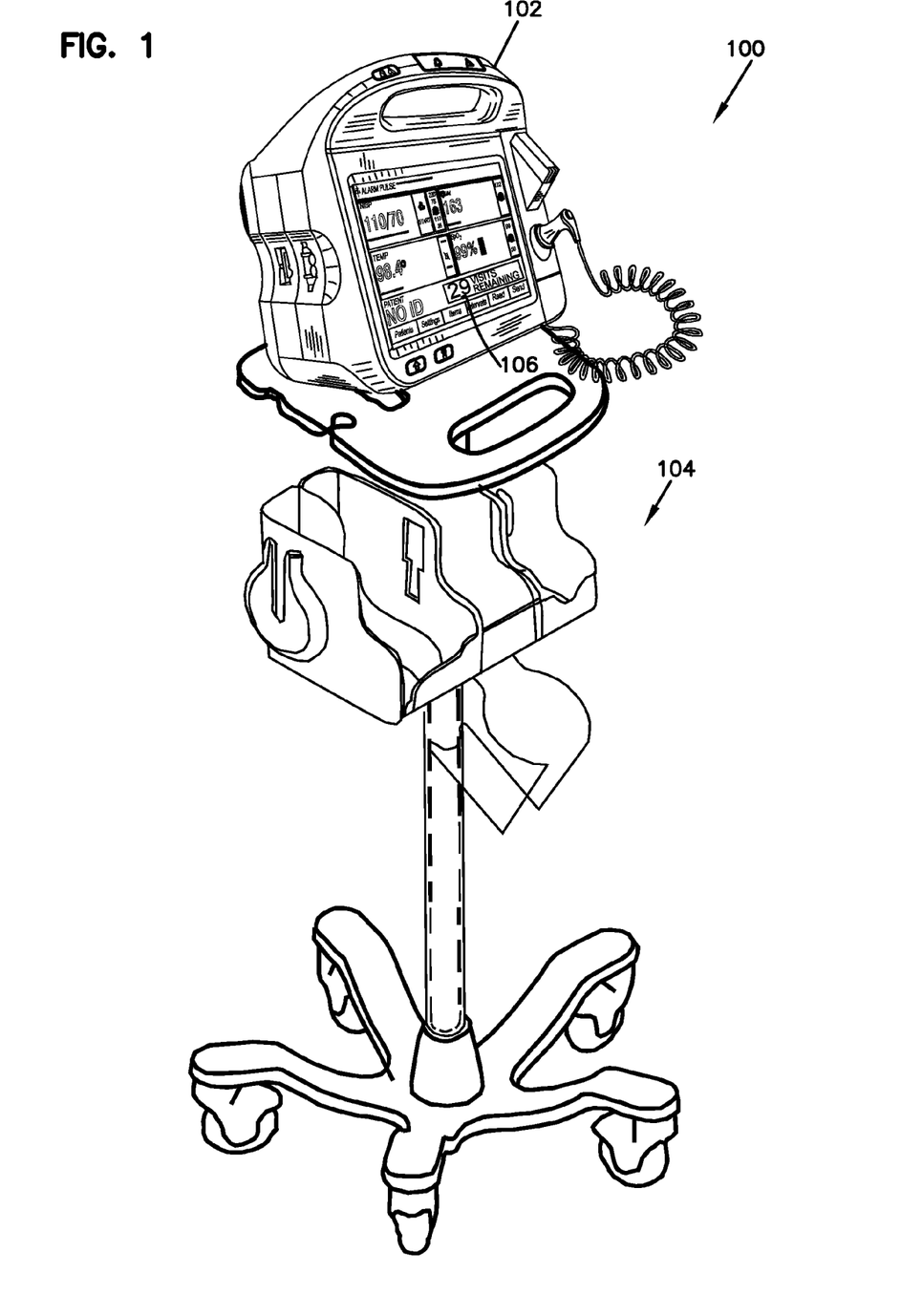
FIG. 1 is a perspective view of an example mobile medical instrument including a measuring device and a mobile stand.

FIG. 1 is a perspective view of an example mobile medical instrument 100. In some embodiments, the mobile medical instrument includes a measuring device 102, and a mobile stand 104. The mobile medical instrument 100 also includes a remaining visits indicator 106.

The mobile medical instrument 100 typically includes a measuring device 102. In some embodiments, the measuring device 102 is a physiological measuring platform device. Some embodiments include a multi-function device configured to perform more than one function. An example of a multi-function device is a physiological measuring platform device that is operable to measure one or more of temperature, heart rate, blood pressure, and blood oxygen level, for example. Examples of the measuring device 102 are illustrated and described in more detail with reference to FIGS. 3-4.

In some embodiments the mobile medical instrument 100 further includes a mobile stand 104. The mobile stand 104 is configured to support the measuring device 102 in an elevated position where a caregiver can more easily interact with it. In some embodiments the mobile stand 104 includes wheels to permit the mobile medical instrument 100 to be easily moved around a health care facility. Examples of the mobile stand 104 are illustrated and described in more detail with reference to FIG. 5.

In the example shown in FIG. 1, the mobile medical instrument 100 includes a remaining visits indicator 106. In some embodiments the remaining visits indicator 106 visually identifies an estimated number of patient visits that can be completed before recharging the medical instrument, as discussed in more detail herein.

Figure 2:
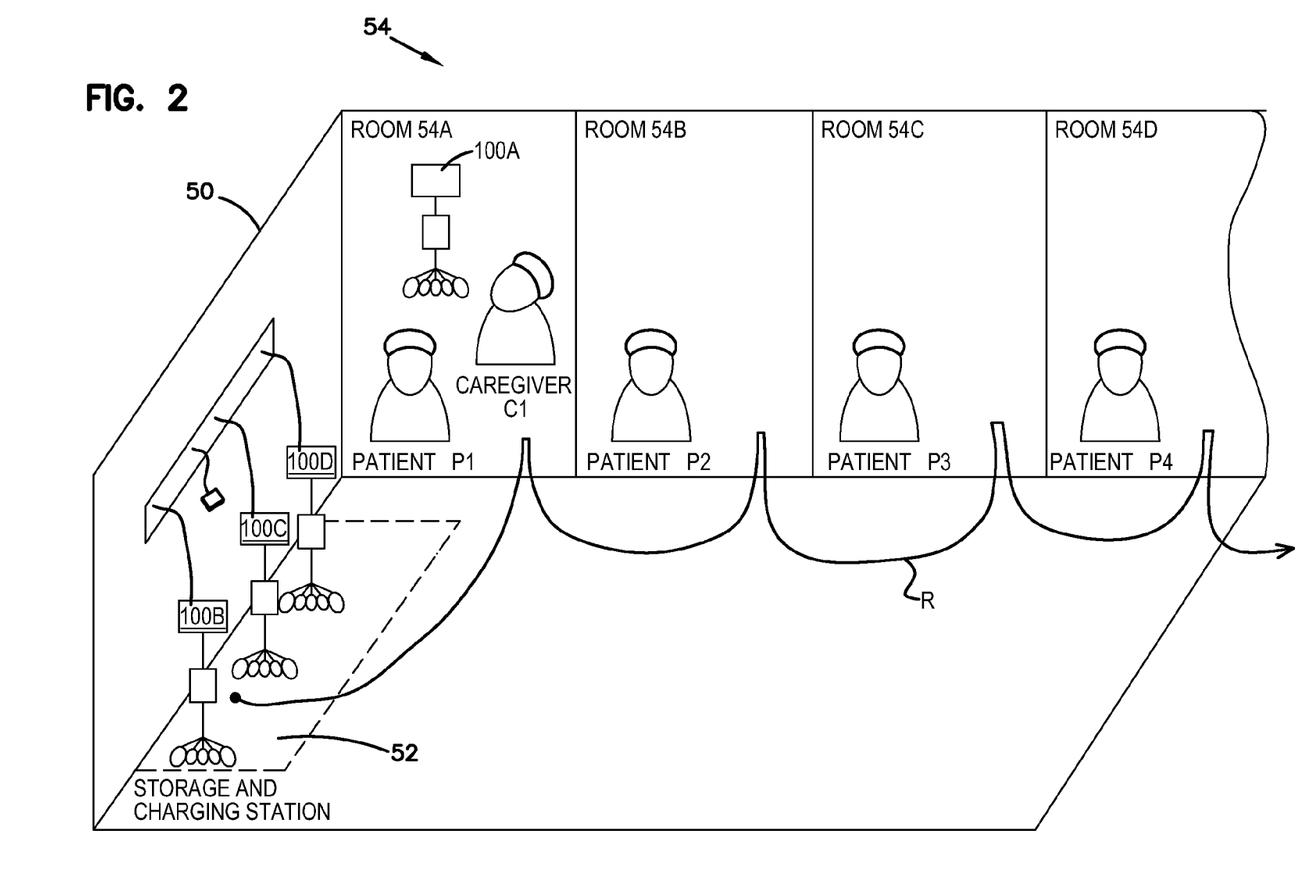
FIG. 2 illustrates an example of a health care facility in which the mobile medical instrument, shown in FIG. 1, can be used.

FIG. 2 illustrates an example of a health care facility 50 to depict one example of an environment in which the mobile medical instrument 100 can be used. In this example, the health care facility 50 is a portion of a building including a storage and charging station 52 and patient rooms 54 (including rooms 54A, 54B, 54C, and 54D). Several mobile medical instruments 100 (including 100A, 100B, 100C, and 100D) are within the health care facility 50. Also shown are patients P1, P2, P3, and P4, and a caregiver C1.

The storage and charging station 52 is a designated space in the health care facility 50 in which the mobile medical instruments 100 are stored when not being used by a caregiver. The storage and charging station 52 is a physical space sufficient to store one or more of the mobile medical instruments 100. In some embodiments the storage and charging station 52 also provides access to a power source that can be used to recharge the mobile medical instruments 100. For example, the charging station 52 can include electrical outlets or cords that can be electrically connected to the mobile medical instruments 100 to provide a connection to mains power. In another possible embodiment, the charging station 52 includes charging electronics configured for connection to and recharging of the mobile medical instruments 100.

The following hypothetical scenario is provided to illustrate an exemplary use of the mobile medical instrument 100. In this example, a caregiver C1 arrives at the health care facility 50 to begin a shift of providing care to a plurality of patients. The caregiver is assigned to perform rounds R to check up on a set of patients, including patients P1, P2, P3, P4, etc.

Before beginning the rounds, the caregiver C1 goes to the storage and charging station 52 to retrieve a mobile medical instrument 100.

If the mobile medical instruments 100 did not have the remaining visits indicator 106 (shown in FIG. 1), it would be difficult for the caregiver C1 to determine whether a mobile medical instrument 100 has sufficient charge remaining to permit the caregiver C1 to complete the rounds R. In some cases, the mobile medical instrument may not have been plugged in by the previous caregiver. Even if the mobile medical instrument is charging, it may have only been charging for a short time. A battery charge indicator does not convey adequate information. Although a battery charge indicator may depict whether the battery is fully charged, partially charged, or nearly depleted, such an indicator does not allow the caregiver to directly determine whether the charge is sufficient to complete the rounds R.

Therefore, the remaining visits indicator 106, such as shown in FIG. 1, is provided to identify the estimated number of patient visits that can be completed before the mobile medical instrument 100 needs to be recharged.

As one example, if the caregiver C1 knows that the rounds R requires the caregiver C1 to visit 25 patients, the caregiver C1 can check the remaining visits indicator 106 and see the number of patient visits that can be completed on the current charge. If the remaining visits indicator 106 shows a number greater than or equal to the number of patients in the rounds R, then the caregiver C1 can determine that he or she can complete the rounds R with the current charge of the mobile medical instrument 100. If the remaining visits indicator 106 shows a number less than the number of patients in the rounds R, then the caregiver C1 can determine that he or she cannot complete the rounds R with the current charge of the mobile medical instrument 100, and should either plan to return part of the way through when the charge is depleted, or should consider taking a different mobile medical instrument 100 that will allow the rounds R to be completed.

In the illustrated example, the caregiver C1 selected the mobile medical instrument 100A to take on the rounds, after checking the remaining visits indicator 106 and determining that the number of remaining visits identified was greater than or equal to the number of patients in the rounds R. This will permit the caregiver C1 to complete the rounds R without having to return to the storage and charging station 52 before the rounds R have been completed.

While on the rounds, the caregiver C1 uses the mobile medical instrument 100 to obtain measurements associated with the patients P. In the illustrated example, the first stop on the caregiver's C1 rounds R is room 54A, which is currently occupied by patient P1. The caregiver enters the room 54A and uses the mobile medical instrument 100A to perform a set of measurements on the patient, such as to check the patient's vital signs. Examples of the vital signs include temperature, heart rate, blood pressure, and blood oxygen level. Other embodiments include other measurements.

Different vital signs measurements require different amounts of charge to complete. For example, a blood pressure reading may require more charge in order to inflate a cuff around the limb of the person to a sufficient pressure, and to operate one or more sensors that detect the patient's heart rate and blood pressure. Accordingly, the amount of charge consumed through the performance of a set of vital signs measurements will vary depending on the particular set of tests that are performed.

Even if the same set of measurements is performed, the amount of charge consumed by the measurements can still vary. Multiple variables can impact the amount of charge consumed, such as how tightly a blood pressure cuff is originally applied, and whether the measurement is repeated one or more times. In some embodiments the mobile medical instrument can include a printer, and different amounts of charge can be consumed depending on whether or not the printer is used after taking measurements for a particular patient. Other functions, such as wireless communication functions and internal processing functions can also adjust charge consumption.

Therefore, in some embodiments the mobile medical instrument 100 stores historical usage data, as discussed in further detail herein, which can be used to determine average charge consumption over a period of time, or across a number of patient visits. This information is then used to predict future usage, so as to permit the mobile medical instrument to predict the number of visits that can be completed before the charge in the mobile medical instrument is depleted.

Figure 3:
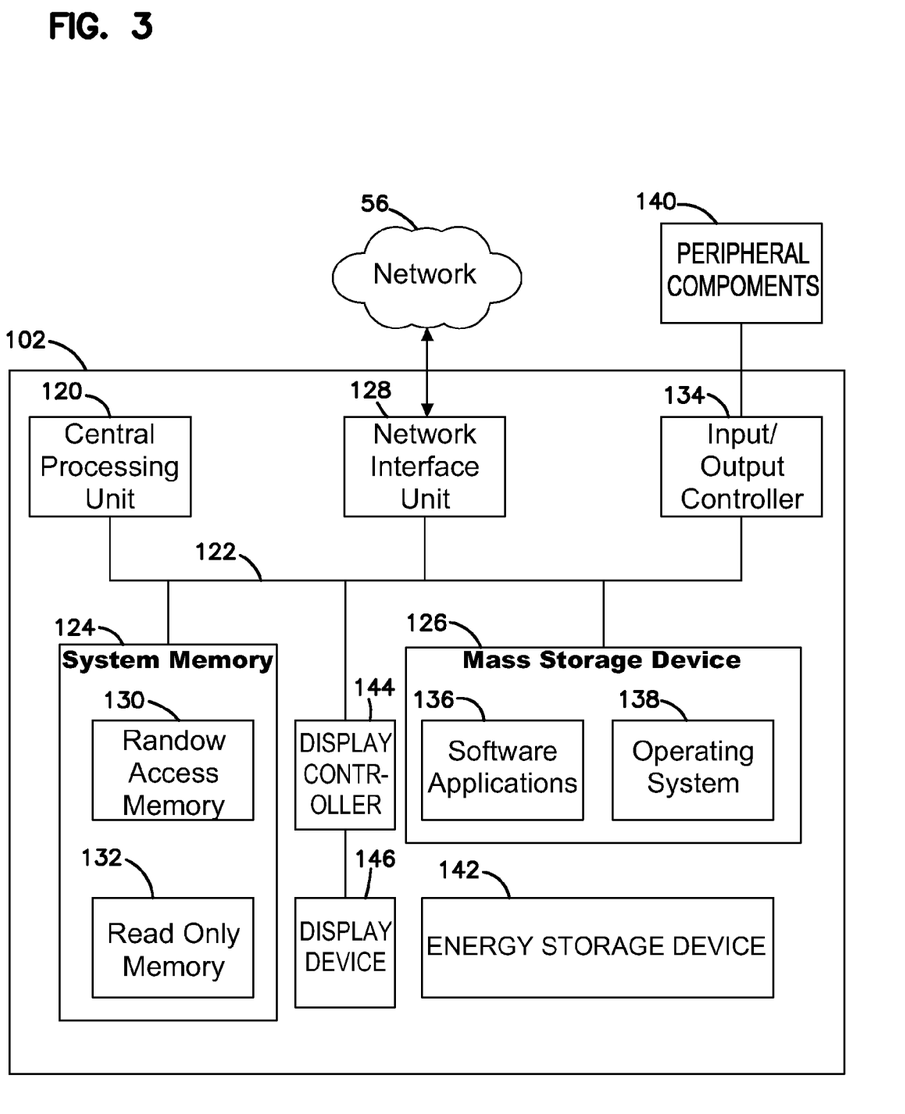
FIG. 3 is a schematic block diagram illustrating an example of the measuring device shown in FIG. 1.
Figure 4:
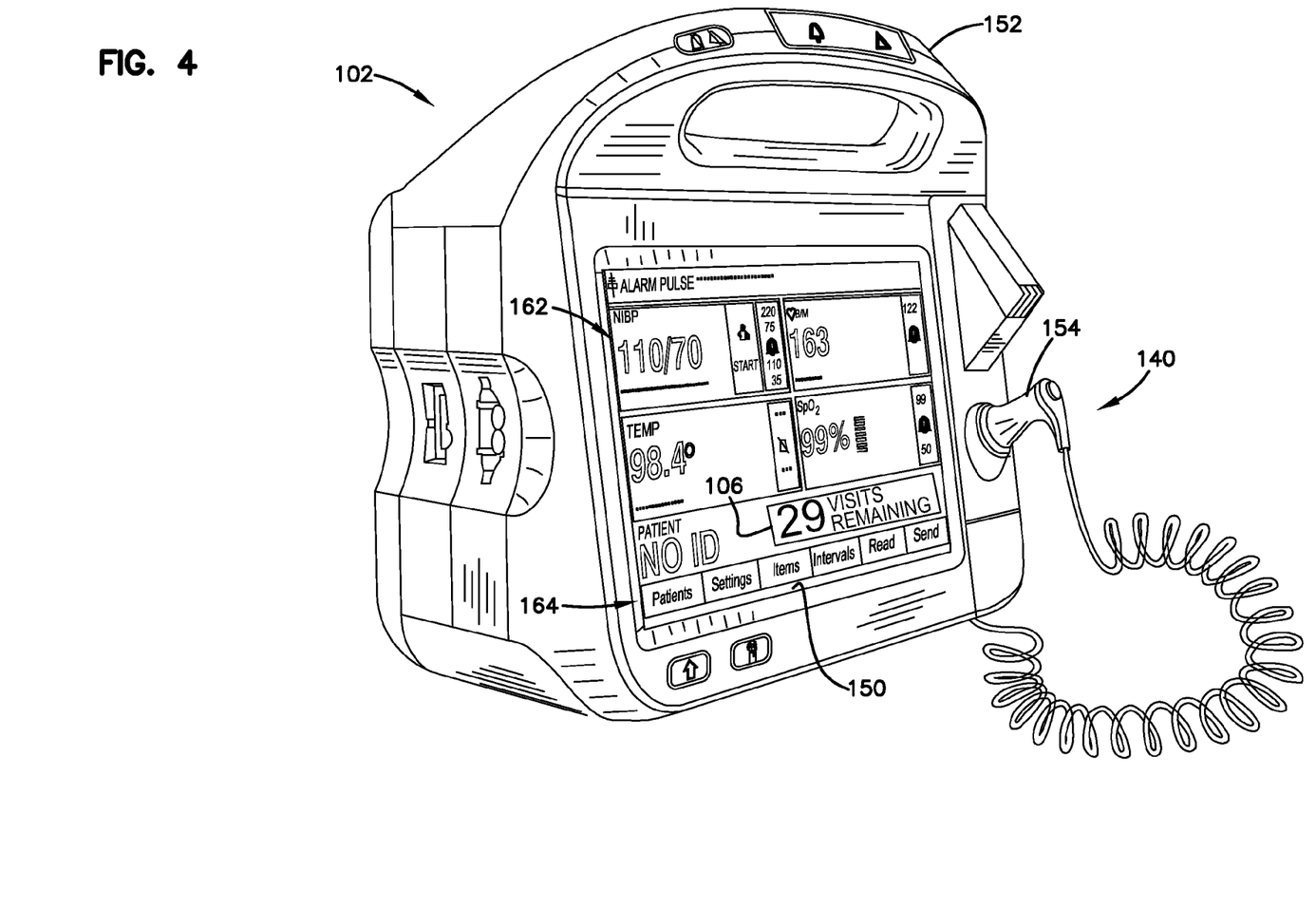
FIG. 4 is a front view of another example of the measuring device shown in FIG. 1.

FIGS. 3-4 illustrate examples of the measuring device 102.

FIG. 3 is a schematic block diagram illustrating an example of the measuring device 102. In this example, the measuring device 102 includes at least one central processing unit ("CPU") 120, a system memory 124, and a system bus 122 that couples the system memory 124 to the CPU 120. The CPU 120 is an example of a processing device. The system memory 124 includes a random access memory ("RAM") 130 and a read-only memory ("ROM") 132. A basic input/output system containing the basic routines that help to transfer information between elements within the measuring device 102, such as during startup, is stored in the ROM 132. The measuring device 102 further includes a mass storage device 126. The mass storage device 126 is able to store software instructions and data.

The mass storage device 126 is connected to the CPU 120 through a mass storage controller (not shown) connected to the bus 122. The mass storage device 126 and its associated computer-readable data storage media provide non-volatile, non-transitory storage for the measuring device 102. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the measuring device 102 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the measuring device 102.

According to various embodiments, the measuring device 102 may operate in a networked environment using logical connections to remote network devices through the network 56, such as a local network, the Internet, or another type of network. The measuring device 102 connects to the network 56 through a network interface unit 128 connected to the bus 122. It should be appreciated that the network interface unit 128 may also be utilized to connect to other types of networks and remote computing systems. The measuring device 102 also includes an input/output controller 134 for receiving and processing input from a number of other devices, such as peripheral components 140. In some embodiments, peripheral components 140 include sensors that can be used by the measuring device 102 to determine one or more physical characteristics of the patient. In some embodiments, the peripheral components 140 are used by the measuring device 102 to perform physiological measurements on the patient. Examples of peripheral components 140 include a thermometer (oral, rectal, temporal, ear, etc.), a blood pressure cuff, and a pulse oximeter. Other peripheral components 140 are used in other embodiments.

In some embodiments the input/output controller 134 is configured to communicate with input devices including a keyboard, a mouse, a touch sensitive user interface display screen, or another type of input device. Similarly, the input/output controller 134 may provide output to a touch sensitive user interface display device 146, a printer, or other type of output device.

As mentioned briefly above, the mass storage device 126 and the RAM 130 of the measuring device 102 can store software instructions and data. The software instructions include an operating system 138 suitable for controlling the operation of the measuring device 102 and software applications 136. The mass storage device 126 and/or the RAM 130 also store software instructions, that when executed by the CPU 120, cause the measuring device 102 to provide the functionality of the measuring device 102 discussed in this document. For example, the mass storage device 126 and/or the RAM 130 can store software instructions that, when executed by the CPU 120, cause the measuring device 102 to display a graphical user interface 150, shown in FIG. 4, including the remaining visits indicator 106, and/or other screens or displays on the display device 146.

In some embodiments the measuring device 102 includes an energy storage device 142. An example of the energy storage device 142 is a rechargeable battery. Rechargeable batteries of a variety of different types can be used. One suitable example is a Lithium-ion type battery. Such batteries can have any desired numbers of cells, and accordingly any desired capacity limited primarily by cost, size, and weight constraints defined for the particular implementation. Another example of the energy storage device 142 is a capacitor, such as a super- or ultra-capacitor.

In some embodiments the energy storage device 142 also includes electronics, such as a processor and electronic circuitry. The central processing unit 120 can communicate with the energy storage device 142 through the electronics to obtain data relating to the energy storage device 142, such as the total energy capacity of the energy storage device 142 and the present charge stored in the energy storage device 142, or alternatively the percentage of the charge that is remaining An example of a suitable energy storage device 142 is any one of the variety of smart battery packs available from Inspired Energy LLC of Newberry, Fla.

In this example the measuring device 102 also includes a display controller 144 and display device 146 that operate to generate a graphical user interface 150, and present that graphical user interface 150 to the caregiver C1, shown in FIG. 2.

FIG. 4 is a front view of an example measuring device 102. In this example, the measuring device 102 includes the peripheral components 140 (such as a thermometer 154) and the display device 146, as previously discussed, and further includes a housing 152.

In this example, the display device 146 generates a graphical user interface 150 that is displayed on a face of the measuring device 102. In some embodiments, the graphical user interface 150 includes measurement displays 162, remaining visits indicator 106, and selectable controls 164.

The measurement display 162 present measurement data obtained through the peripheral components 140. In this example, the measurement display 162 shows the blood pressure, heart rate, temperature, and SpO2 measurement data. Other measurement data is displayed in other embodiments.

The remaining visits indicator 106 identifies the number of patient visits that can be completed on the present charge (e.g., stored in the energy storage device 142, shown in FIG. 3), before the mobile medical instrument 100 will need to be recharged. The remaining visits indicator 106 is discussed in further detail herein.

The selectable controls 164 provide a menu for accessing other possible functions of the measurement device, such as to change settings, alarms, intervals, or calibration, or to send measurement data through the network 56, shown in FIG. 3.

Figure 5:
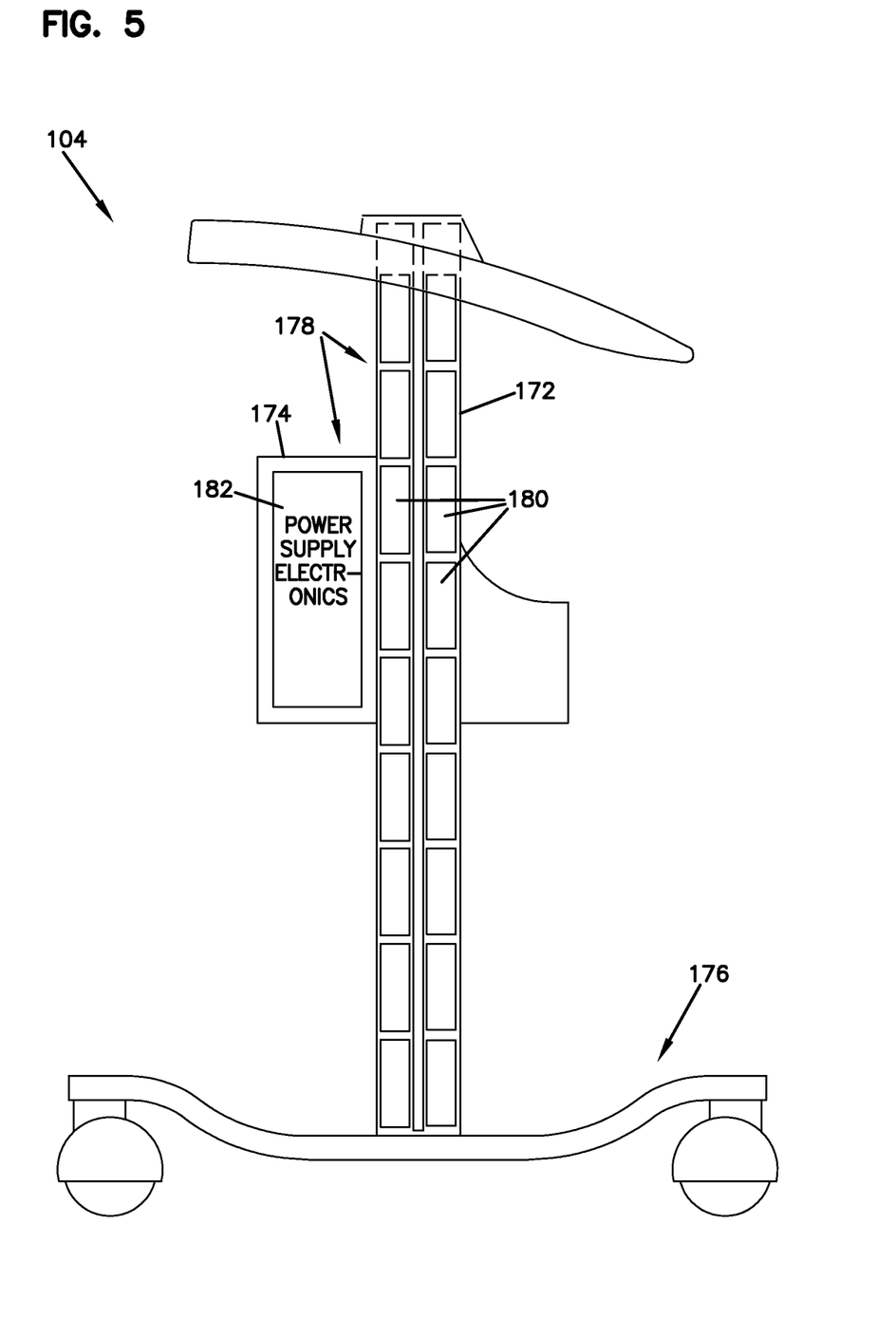
FIG. 5 is a schematic diagram illustrating an example of the mobile stand shown in FIG. 1.

FIG. 5 is a schematic diagram illustrating an example of the mobile stand 104. In this example, the mobile stand 104 includes a support structure 172, a storage region 174, and a wheeled base 176. In addition, in some embodiments the mobile stand 104 includes an integral power supply 178.

In some embodiments, the mobile stand 104 operates to support the measuring device 102 in an elevated position above the ground. To do so, the measuring device 102 is placed on the mobile stand 104 and fastened thereto, as shown in FIG. 1. The support structure 172 supports the measuring device 102 in the elevated position.

A wheeled base 176 is provided in some embodiments to permit the mobile medical instrument 100 to be easily moved within a health care facility 50, such as shown in FIG. 2. The wheeled base 176 includes one or more wheels. The support structure 172 is connected to the wheeled base 176.

A storage region 174 is provided in some embodiments for the storage of additional items, such as peripheral components, medical records, or any other items. In some embodiments the storage region 174 also includes an interior space in which portions of the power supply 178 can be housed.

In some embodiments the mobile stand 104 includes an integral power supply 178, which stores electrical energy that can be used to power the measuring device 102. The power supply 178 includes one or more energy storage devices 180 that store electrical energy. Examples of the energy storage devices 180 are batteries and capacitors.

In some embodiments the energy storage devices 180 are housed within an interior space of the support structure 172, or alternatively within an interior space of the storage region 174, or both.

Some embodiments further include power supply electronics 182. In some configurations, the power supply electronics 182 include a processing device that monitors the status of the energy storage devices 180, such as to identify the capacity of the energy storage devices 180 and a charge level of the energy storage devices 180. In some embodiments the measuring device 102 communicates with the power supply electronics 182, such as through wired or wireless connections, to obtain data relating to the energy storage devices 180.

One example of a suitable mobile stand 104 is described in U.S. Ser. No. 13/718,869, filed on Dec. 18, 2012, titled MOBILE CART WITH CAPACITIVE POWER SUPPLY, the disclosure of which is hereby incorporated by reference in its entirety.

Although in the example shown in FIG. 5 the power supply electronics 182 are illustrated as being located within the storage region 173, the power supply electronics 182 (or other electronic components discussed herein) can be arranged in other locations within the mobile stand 104 or measuring device 102. For example, in some embodiments electronics are arranged within the upper work surface of the mobile stand 104.

Figure 6:
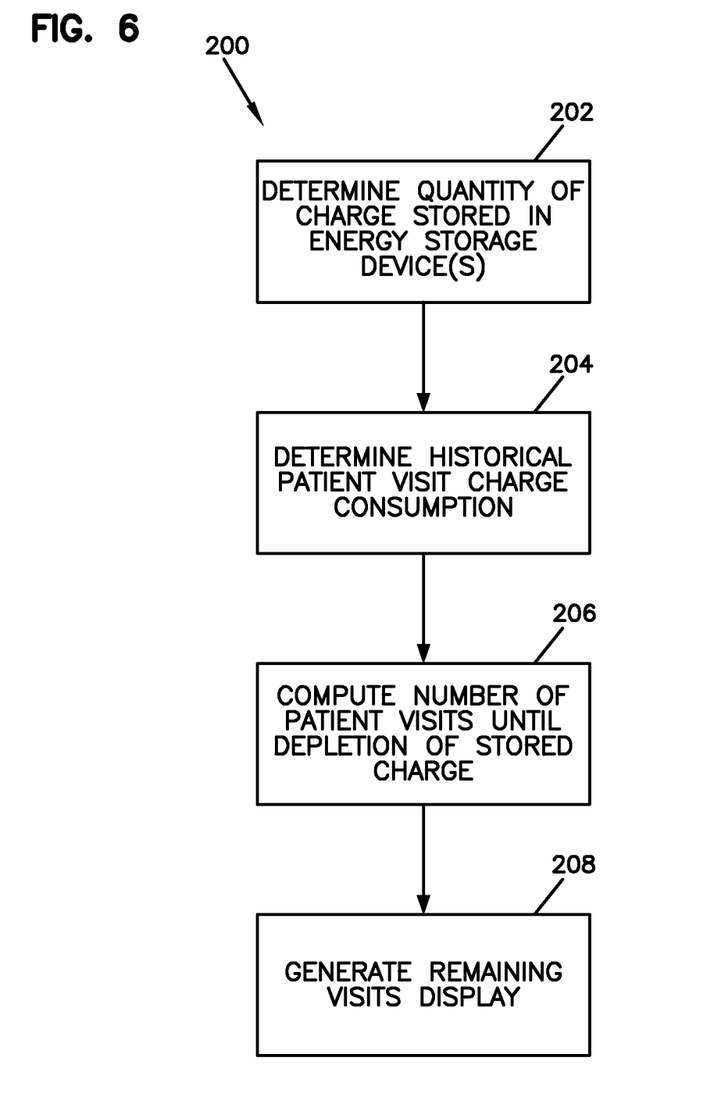
FIG. 6 is a flow chart illustrating a method of operating the mobile medical instrument shown in FIG. 1.

FIG. 6 is a flow chart illustrating a method 200 of operating a mobile medical instrument 100. In this example, the method includes operations 202, 204, 206, and 208.

The operation 202 is performed to determine a quantity of charge store in one or more energy storage devices. An example of operation 202 is illustrated and described in more detail with reference to FIG. 7.

The operation 204 is performed to determine historical patient visit charge consumption. Examples of operation 204 are illustrated and described in more detail with reference to FIGS. 8-9.

The operation 206 is performed to compute an estimated number of patient visits that can be completed using the mobile medical instrument until the stored charge is depleted. An example of the operation 206 is illustrated and described in more detail with reference to FIG. 10.

The operation 208 is performed to generate a remaining visits indicator. An example of the remaining visits indicator 106 is shown in FIG. 4.

In some embodiments, one or more of the operations 202, 204, 206, and 208 are performed using a processing device, such as a processing device of the measuring device 102 or of the mobile stand 104, shown in FIG. 1. The remaining visits indicator 106 is displayed on a display device of the mobile medical instrument 100, such as of the measuring device 102 or of the mobile stand 104.

In some embodiments, the remaining visits indicator 106 is part of the mobile stand 104. For example, the remaining visits indicator 106 is arranged in or adjacent a handle (shown in FIG. 1) of the mobile stand 104. The remaining visits indicator 106 can be implemented with a variety of different display devices, such as an LCD or LED panel display device. A LED text display including multi-segment LEDs is used in some embodiments. Any other display technology can also be used in other embodiments. In some embodiments the remaining visits indicator 106 is coupled with one or more other indicators, which may be provided adjacent to one another, or may be combined into the single display, such as by cycling through multiple different indicators through the same display. For example, in some embodiments the indicator also displays one or more of: a battery power remaining, an estimated amount of time remaining, and a date/time indicator. Some embodiments include the remaining visits indicator 106 along with a date and/or time indicator. In some embodiments multiple indicators are contained in and included in single display.

Figure 7:
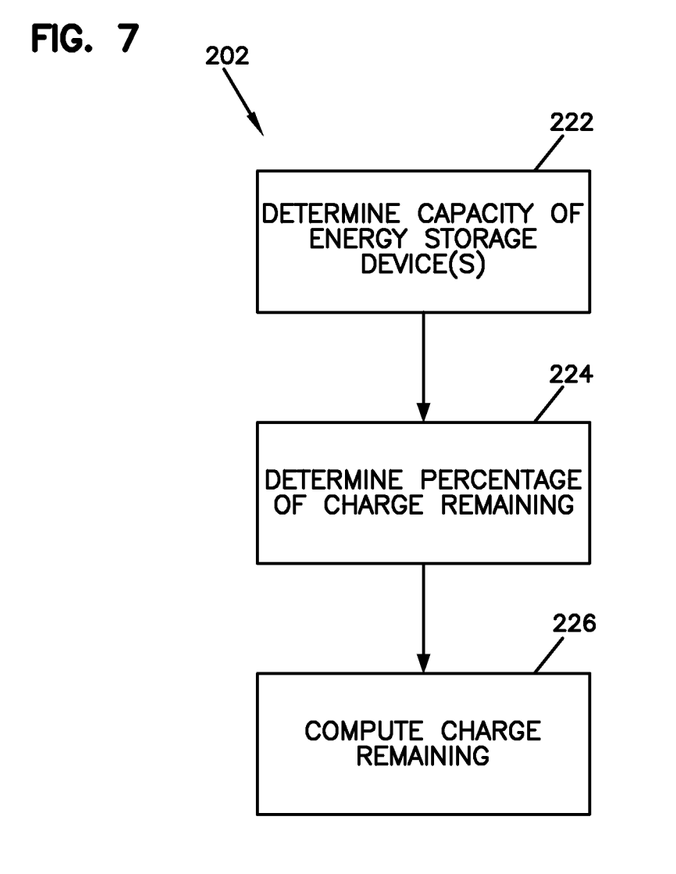
FIG. 7 is a flow chart illustrating a method of determining a quantity of charge stored in one or more energy storage devices.

FIG. 7 is a flow chart illustrating a method 202 of determining a quantity of charge stored in one or more energy storage devices. FIG. 7 also illustrates an example of the operation 202, shown in FIG. 6. In this example, the method 202 includes operations 222, 224, and 226.

The operation 222 is performed to determine a capacity of one or more energy storage device(s) that are available to supply power to the mobile medical instrument 100. In some embodiments, operation 222 involves querying the energy storage devices, such as by sending a message to the energy storage device 142, shown in FIG. 3, and/or to the energy storage device 180, shown in FIG. 5. In some embodiments, the energy storage devices provide their capacities in response. In other embodiments, the energy storage devices provide an identifier of a type of the energy storage device, which permits the mobile medical instrument to determine the capacity, such as using a lookup table that maps types of energy storage devices with their capacities. For example, in some embodiments the energy storage devices can include various numbers of cells, such as 3, 5, 7, or 9 cells. Each cell has a known capacity, and therefore once the type of energy storage device is known, and the number of cells in that type, the capacity can be determined.

The operation 224 is performed to determine a percentage of charge remaining in the energy storage device(s). In some embodiments, operation 224 involves querying the energy storage devices, such as by sending a message to the energy storage device 142, shown in FIG. 3, and/or to the energy storage device 180, shown in FIG. 5, requesting that the energy storage devices identify the current percentage of charge remaining In some embodiments, the energy storage devices reply with a percentage of charge remaining The operation 226 is performed to compute the charge remaining in the energy storage device(s). As one example, the operation 226 multiplies the capacity from operation 222 by the percentage of charge remaining to determine the total charge remaining in the energy storage device. When multiple energy storage devices are present, the total charge remaining is computed as the sum of the individual charges remaining in each of the energy storage devices. A stored charge value is stored in a computer readable storage device that identifies the total charge stored in the energy storage devices.

Figure 8:
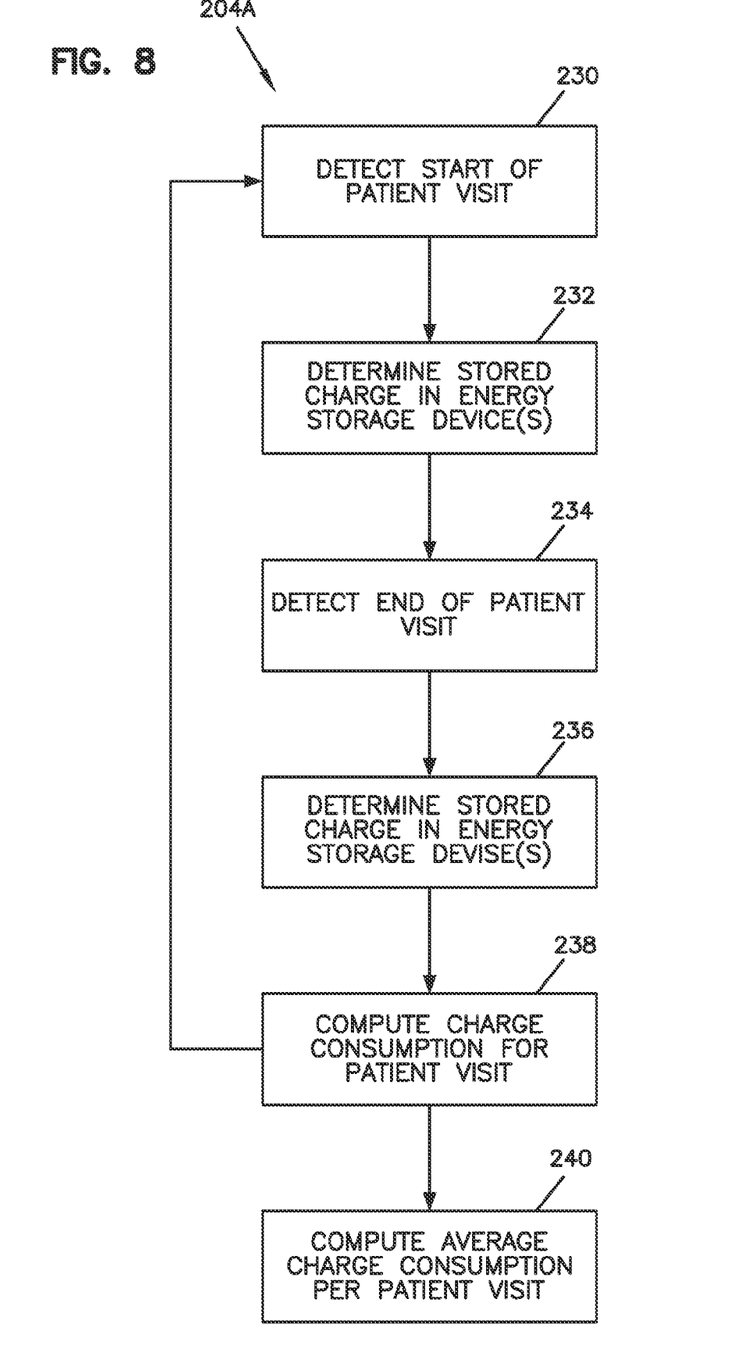
FIG. 8 is a flow chart illustrating an example method of determining historical patient visit charge consumption.

FIG. 8 is a flow chart illustrating an example method 204A of determining historical patient visit charge consumption. FIG. 8 is also an example of the operation 204, shown in FIG. 7. In this example, the method 204A includes operations 230, 232, 234, 236, 238, and 240.

The operations 230, 232, 234, 236, and 238 are performed to evaluate the charge consumption during an individual patient visit. The operation 240 is then performed to use this data to determine an average charge consumption per patient visit.

The operation 230 is performed to detect the start of a patient visit. In some embodiments, the start of a patient visit occurs when the caregiver C1 (shown in FIG. 2) provides an input into the mobile medical instrument, such as by pressing a physical button or selectable control on the measuring device 102. In some embodiments, the mobile medical instrument 100 operates in a sleep mode (e.g., a low power consumption mode) when not in use, and the mobile medical instrument 100 returns to the normal operating mode upon receipt of an input from the caregiver C1.

In some embodiments, after detection of the start of the patient visit in the operation 230, the operation 232 is performed to determine the amount of charge stored in the energy storage device(s). One possible process for doing so is illustrated in FIG. 7. The stored charge value representing the amount of charge stored at the beginning of the patient visit is then stored in a computer readable storage device for subsequent use.

The mobile medical instrument 100 is then operated to perform the desired functions as directed by the caregiver C1, such as to take one or more measurements using the peripheral components 140 and measuring device 102. As the functions are performed, energy is consumed from the energy storage devices.

The operation 234 is performed to detect the end of a patient visit. There are multiple different ways that the end of a patient visit can be determined. One possible way is to detect that a predetermined period of time (such as in a range from about 1 minute to about 5 minutes) has elapsed without receiving any inputs from the caregiver C1 into the mobile medical instrument 100. Once the predetermined period of time has elapsed, the mobile medical instrument 100 determines that the patient visit has been completed. In some embodiments, the mobile medical instrument 100 returns to a sleep mode of operation after the predetermined period of time has elapsed.

In another possible embodiment, the mobile medical instrument detects the receipt of an input from a caregiver C1. The input can be, for example, the selection of a power button, a sleep button, or an end button, any of which signal to the mobile medical instrument that the caregiver C1 has completed the patient visit.

In yet another possible embodiment, the mobile medical instrument 100 includes an accelerometer which operates to detect movement of the mobile medical instrument. Typically during a patient visit the mobile medical instrument 100 will be substantially stationary. At the end of the patient visit, the caregiver C1 will move the mobile medical instrument 100 from one room (such as room 54A, shown in FIG. 2) to another room (such as room 54B, shown in FIG. 2). In order to avoid incorrect determinations of the end of the patient visit, the operation 234 can monitor the movement data from the accelerometer to identify movement that occurs for more than a predetermined period of time (e.g., in a range from about 3 seconds to about 30 seconds), and/or greater than a predetermined magnitude. Once movement is detected that satisfies the predefined criteria, the mobile medical instrument 100 determines that the patient visit has ended.

The accelerometer can also or alternatively be used for other purposes. For example, in some embodiments the remaining visits indicator 106 is activated upon the detection of movement (including pulling, tapping, shaking, nudging, etc.) of the mobile medical instrument 100, by the accelerometer.

In other embodiments, the remaining visits indicator 106 is activated by a touch or proximity sensor, for example. When not activated, the remaining visits indicator 106 can be turned off, or placed into a low power sleep mode to conserve energy. In some embodiments the remaining visits indicator is displayed by a display device separate from a primary user interface display device of the measuring device 102.

In some embodiments the remaining visits indicator 106 can be displayed separate from the measuring device 102. An advantage of the separate display is that the remaining visits indicator 106 can be displayed promptly upon the receipt of an input, without having to wait for the measuring device 102 to be powered on and complete a boot process, for example. Instead, the remaining visits indicator 106 can be immediately displayed upon the receipt of an input, which can include detected movement, a tap input onto the remaining visits indicator, pressing or selecting a button, switch, or other input device, and the like. This allows the caregiver to quickly determine the number of remaining visits available on the mobile medical instrument 100, to determine whether the remaining visits are adequate for his or her needs, or whether a different mobile medical instrument 100 should be selected.

At the conclusion of the patient visit, operation 236 is performed to determine the amount of charge stored in the energy storage device(s). One possible process for doing so is illustrated in FIG. 7. The stored charge value representing the amount of charge stored at the end of the patient visit is stored in a computer readable storage device for subsequent use.

When the process of operations 230, 232, 234, 236, and 238 is repeated, as graphically illustrated in FIG. 8, the determination of the stored charge in both of operations 232 and 236 is not required. Instead, in some embodiments only one of operations 232 and 236 can be performed. For example, the result of operation 236 can also be identified and used as the starting charge (operation 232) for the next patient visit.

The operation 238 is performed to compute the charge consumption for the concluded patient visit. As one example, the stored charge value at the end of the patient visit (operation 236) is subtracted from the stored charge value at the start of the patient visit (operation 232). The difference represents the amount of charge consumed during the patient visit. The charge consumption value representing the amount of charge consumed during the patient visit is stored in a computer readable storage device.

The process involving some or all of operations 230, 232, 234, 236, and 238 is repeated for each subsequent patient visit to generate historical patient visit charge consumption data.

Once the historical patient visit charge consumption data has been generated, the operation 240 is performed to compute an average charge consumption per patient visit. In one example, the historical patient visit charge consumption data is evaluated over a set of patient visits to determine an average charge consumption per patient visit. As one example, a set of the 10 most recent patient visits is evaluated. Other embodiments use other set sizes, such as in a range from about 3 to about 30 or more. An average charge consumption value is stored in a computer readable storage device identifying the average charge consumed per patient visit.

Other factors can also be considered in other embodiments. Several examples of other factors include the time of day, the identity of the current caregiver C1 operating the mobile medical instrument, and an identified set of tests and measurements that are to be performed during the rounds R (FIG. 2).

Figure 9:
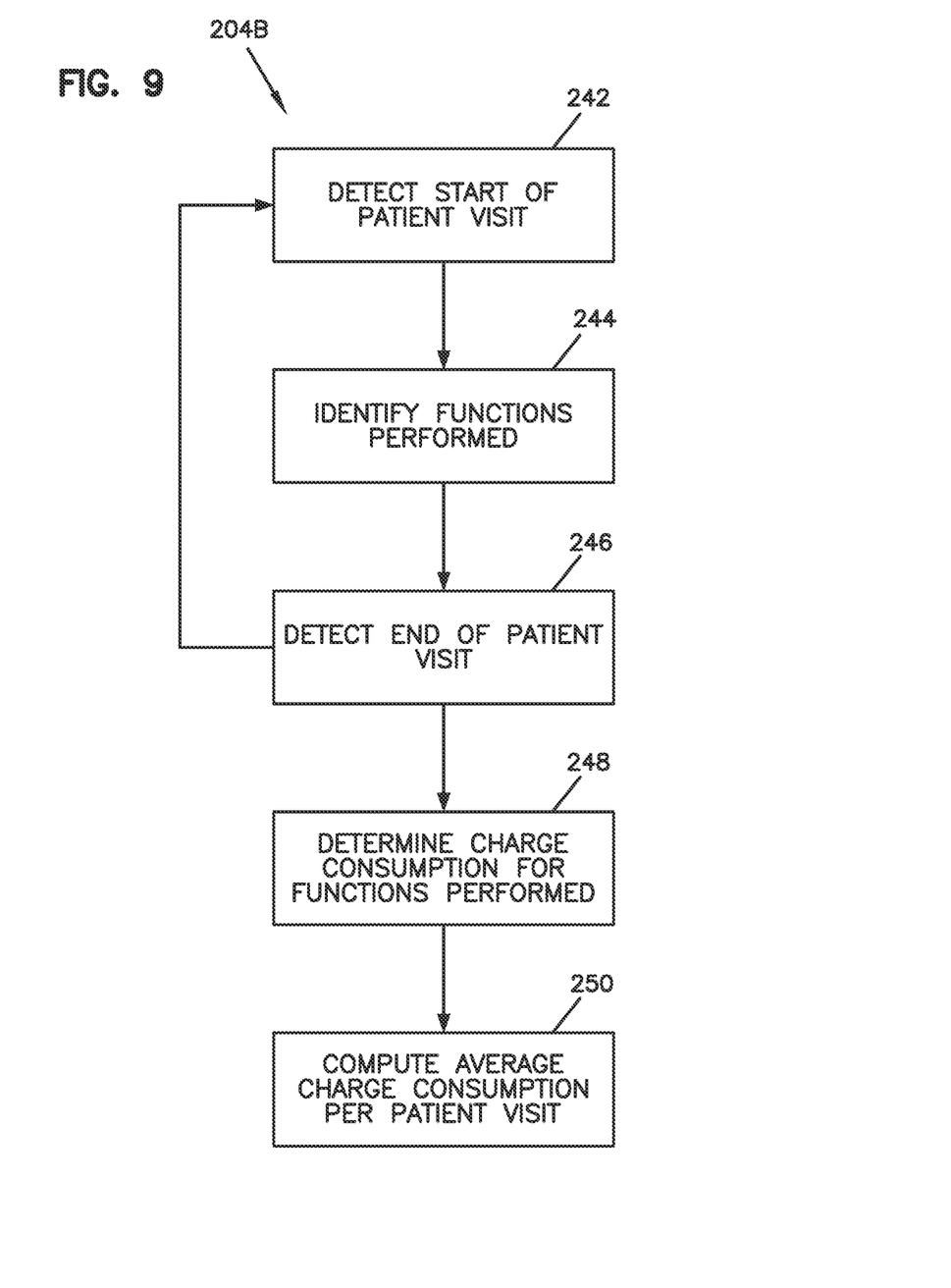
FIG. 9 is a flow chart illustrating another method of determining historical patient visit charge consumption.

FIG. 9 is a flow chart illustrating another method 204B of determining historical patient visit charge consumption. FIG. 9 is also another example of the operation 204, shown in FIG. 7. In this example, the method 204B includes operations 242, 244, 246, 248, and 250.

In this example, rather than determining the charge consumption of each patient visit directly, operations 242, 244, and 246 operate to identify a set of functions performed by the mobile medical instrument during a patient visit. Using this information, a typical set of functions that are performed during a patient visit can be identified. Once the typical set of functions is known, the charge consumption can be determined in operation 248, such as by retrieving an estimated charge consumption value for each of these functions from a lookup table, or alternatively from historical data. An average charge consumption per patient visit is then computed in operation 250 based on the typical set of functions that are performed.

Figure 10:
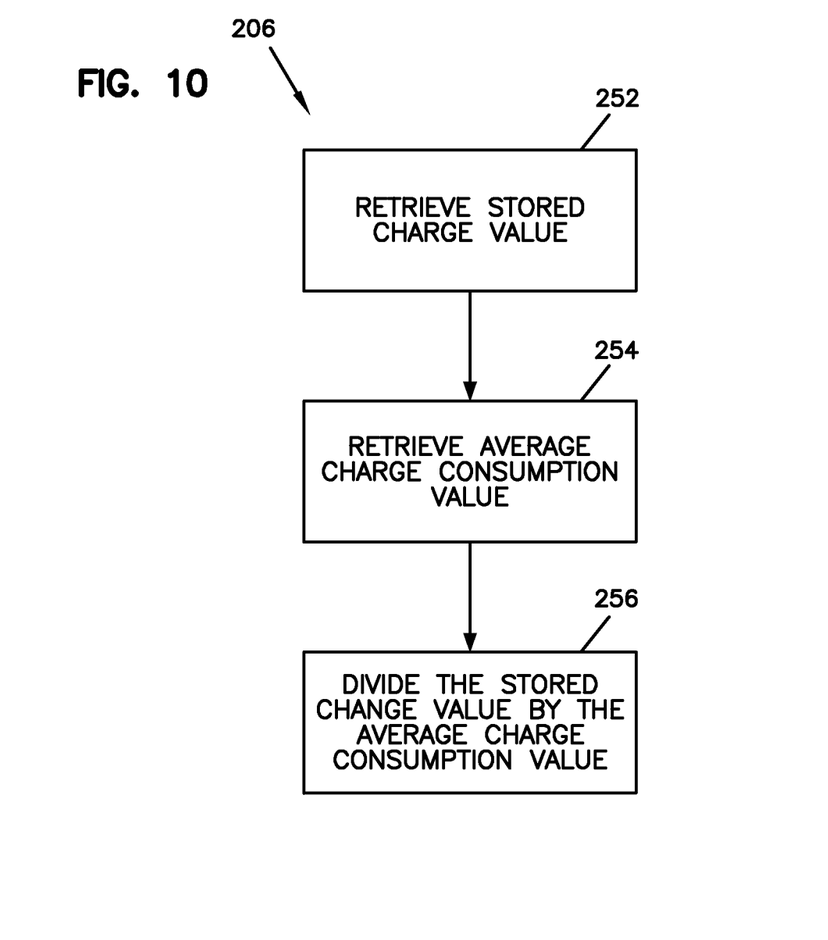
FIG. 10 is a flow chart illustrating an example method of computing a number of patient visits that can be completed before the stored charge is depleted.

FIG. 10 is a flow chart illustrating an example method 206 of computing an estimated number of patient visits that can be completed before the stored charge is depleted, and before recharging is needed. FIG. 10 is also an example of the operation 206, shown in FIG. 6. In this example, the method 206 includes operations 252, 254, and 256.

The operation 252 is performed to retrieve the stored charge value from the computer readable storage device. The stored charge value indicates the amount of charge currently stored in the energy storage device(s), such as determined using the operation 202, shown in FIG. 6.

The operation 254 is performed to retrieve the average charge consumption value from the computer readable storage device. The average charge consumption value indicates the average charge consumed per patient visit, such as determined using the operation 204, shown in FIG. 6

The operation 256 is performed to compute the number of patient visits remaining on the current charge. In one example, the computation occurs by dividing the stored charge value by the average charge consumption value to generate an estimate of the number of patient visits that can be completed by the mobile medical instrument on the current charge.

Once the estimated number of patient visits remaining has been computed, the remaining visits indicator 106 can be generated as represented by operation 208, shown in FIG. 6. An example of the remaining visits indicator 106 is shown in FIG. 3. The remaining visits indicator 106 can be presented anywhere on the mobile medical instrument 100, such as through the graphical user interface 150 of the measuring device 102, or on a separate display of the measuring device 102 or mobile stand 104. In some embodiments the remaining visits indicator 106 is displayed by an electronic display device including an electronic paper display. Other display devices are used in other embodiments.

In some embodiments, the remaining visits indicator 106 is visible whether or not the mobile medical instrument 100 is plugged into the charging station or not. In some embodiments the remaining visits indicator 106 is illuminated continuously when the mobile medical instrument 100 is plugged in, but flashes when not plugged in to conserve energy. As one example, the display flashes at a rate of $\frac{1}{5}^{th}$ of a second. In some embodiments the remaining visits indicator 106 has a different graphical presentation when the remaining number of patient visits available on the current charge is reduced below a predetermined value. As one example, the remaining visits indicator 106 is backlit with a multi-colored (e.g., two or more) LED, such that a second color (e.g., red) is illuminated when the number of remaining patient visits goes below the threshold value.

In some embodiments the remaining visits indicator graphically displays a numerical value. In other embodiments, the remaining visits indicator conveys a number in a non-numerical form. One example of a non-numerical form is the illumination of a number of LEDs, where each illuminated LED represents one remaining patient visit. A graphical user interface can similarly display dots or other non-numerical graphical elements representing remaining patient visits, in yet other embodiments.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A mobile medical instrument configured for use by a caregiver during patient visits, the mobile medical instrument comprising:
    a measuring device configured to perform physiological measurements on patients during the patient visits;
    one or more energy storage devices configured to store energy therein to power the measuring device when performing the physiological measurements, the stored energy depleted by performance of the physiological measurements during patient visits comprising patient visit charge consumption;
    a memory storage device configured to store a history of patient visit charge consumption;
    a processing device configured to determine an average charge consumption per patient visit based on the stored history of patient visit charge consumption; and
    a display device configured to generate a remaining visits indicator based on the average charge consumption, the remaining visits indicator displaying a numeric value indicating an estimated number of patient visits that can be completed by the instrument before the energy stored in the one or more energy storage devices is depleted.

2. The mobile medical instrument of claim 1, wherein the measuring device is a physiological measuring platform device.

3. The mobile medical instrument of claim 2, wherein the physiological measuring platform device is a multi-function device configured to perform more than one function.

4. The mobile medical instrument of claim 3, wherein the more than one functions are selected from a temperature measurement, a heart rate measurement, a blood pressure measurement, and a blood oxygen level measurement.

5. The mobile medical instrument of claim 1, wherein the measuring device includes peripheral components.

6. The mobile medical instrument of claim 5, wherein the peripheral components include a thermometer, a blood pressure cuff, and a pulse oximeter.

7. The mobile medical instrument of claim 1, wherein the display device is part of the measuring device.

8. The mobile medical instrument of claim 1, further comprising mobile stand, and wherein the display device is part of a mobile stand.

9. The mobile medical instrument of claim 1, wherein the display device comprises electronic paper.

10. The mobile medical instrument of claim 1, further comprising a mobile stand, the mobile stand comprising:
a wheeled base including a plurality of wheels; and
a support structure supported on the wheeled base, wherein the support structure is configured to support the measuring device in an elevated position.

11. The mobile medical instrument of claim 10, wherein the mobile stand further comprises:
energy storage devices housed in the support structure; and
power supply electronics electrically coupled to the energy storage devices, wherein the power supply electronics include the processing device, the processing device configured to communicate with the measuring device.

12. The mobile medical instrument of claim 1, wherein the display device is separate from the measuring device, and further comprising an input device, wherein the display device is operable to generate the remaining visits indicator after receipt of an input through the input device independent of whether the measuring device is turned on or off.

13. The mobile medical instrument of claim 1, wherein the average charge consumption per patient visit is determined based on a predetermined set size of patients.

14. The mobile medical instrument of claim 1, wherein the patient visit charge consumption is determined based on a difference in charge between a stored charge value at the start of a patient visit and a stored charge value at the end of the patient visit.

15. The mobile medical instrument of claim 14, wherein the start of a patient visit is indicated by a caregiver first input to the mobile medical instrument.

16. The mobile medical instrument of claim 14, wherein the end of a patient visit is indicated by an elapsed amount of time from the start of the patient visit.

17. The mobile medical instrument of claim 14, wherein the end of a patient visit is indicated by a caregiver second input to the mobile medical instrument.

18. The mobile medical instrument of claim 14, wherein the end of a patient visit is indicated by movement of the mobile medical instrument.

19. The mobile medical instrument of claim 18, further comprising an accelerometer and wherein the movement of the mobile medical instrument is detected by the accelerometer.

20. The mobile medical instrument of claim 1, wherein the patient visit charge consumption is determined based on predetermined set of the physiological measurements performed on patients during the patient visits, wherein each physiological measurement of the predetermined set corresponds to a charge consumption value.

21. The mobile medical instrument of claim 1, wherein the numeric value of the average charge consumption-based remaining visits indicator is calculated by the processing device by dividing a current stored charge value of the one or more energy storage devices by the average charge consumption per patient visit.

* * * * *